United States Patent [19]
Cohen et al.

[11] Patent Number: 5,908,925
[45] Date of Patent: Jun. 1, 1999

[54] GENETICALLY ENGINEERED IMMUNOGLOBULINS WITH SPECIFICITY FOR GLYCATED ALBUMIN

[75] Inventors: Margo P. Cohen, New York, N.Y.; Clyde W. Shearman, West Chester, Pa.

[73] Assignee: Exocell, Inc., Philadelphia, Pa.

[21] Appl. No.: 08/672,176

[22] Filed: Jun. 27, 1996

[51] Int. Cl.⁶ .......................... C07H 21/04; C07H 16/00; A61K 39/395
[52] U.S. Cl. .................. 536/23.53; 530/388.25; 424/133.1
[58] Field of Search ................ 536/23.53; 530/388.25; 424/133.1

[56] References Cited

U.S. PATENT DOCUMENTS

| | | |
|---|---|---|
| 5,091,513 | 2/1992 | Huston et al. . |
| 5,223,392 | 6/1993 | Cohen . |
| 5,518,720 | 5/1996 | Cohen . |
| 5,530,101 | 6/1996 | Queen et al. . |

OTHER PUBLICATIONS

Cohen et al (J. Clin. Inv. vol. 95 pp. 2338–2345), May 1995.
Dixon *Advances in Immunology* Academic Press vol. 44 pp. 65–92, 1989.

*Primary Examiner*—Anthony C. Caputa
*Assistant Examiner*—Mark Navarro
*Attorney, Agent, or Firm*—Caesar, Rivise, Bernstein, Cohen & Pokotilow, Ltd.

[57] ABSTRACT

This invention deals with genetically engineered immunoglobulins with affinity and specificity for (human) glycated albumin. The invention is directed to the DNA which encodes the immunoglobulins. The DNA sequence can be manipulated to produce chimeras and fragments such as Fab, F(ab')$_2$ or ScFv. The immunoglobulins can be produced by recombinant DNA methods and readily purified. The invention also provides a novel and improved method for treating the complications of diabetes.

4 Claims, 4 Drawing Sheets

Fig. 1

T7 Terminator huA717VL   Linker   huA717VH

GENETICALLY ENGINEERED IMMUNOGLOBULINS WITH SPECIFICITY FOR GLYCATED ALBUMIN

BACKGROUND OF THE INVENTION

The direct relationship between hyperglycemia and nonenzymatic glycation, the condensation between free glucose and reactive protein amino groups that is accelerated in diabetes, has implicated this reaction in the development of diabetic complications. Experimental studies have shown that albumin modified by Amadori glucose adducts has distinct biologic effects that unmodified albumin does not possess. Renal glomeruli isolated from normal rats exhibit preferential uptake of glycated albumin relative to nonglycated albumin, which is accompanied by an increase in cell hydrogen peroxide production, and this abnormality can be duplicated in glomerular cells from normal rats by injecting glycated albumin and raising its circulating concentration (Daniels et al, *J Am Soc Nephrol* 4:791A, 1993). Normal rats transfused with glycated serum proteins containing Amadori products of the glycation reaction in concentrations similar to those found in streptozotocin diabetic rats manifest hyperfiltration, a functional abnormality observed early in the development of diabetic nephropathy (Sabbatini et al, *Kidney Int* 42:875, 1992). Human sera containing diabetic concentrations of glycated albumin stimulate mesangial cell synthesis and gene expression of type IV collagen, the principal constituent of the expanded extracellular matrix observed in the diabetic renal glomerulus (Cohen and Ziyadeh, *Kidney Int* 45:475, 1994; Ziyadeh and Cohen, *Mol Cell Biochem* 125:19, 1993; Cohen et al, *Mol Cell Biochem* 151:61, 1995). The glycated albumin-induced in vitro effects on mesangial cell biology mimic the changes that characterize human diabetic nephropathy, are likely mediated by ligand-receptor systems that recognize the glucose-modified epitope in glycated albumin, and can be prevented by molecules capable of reacting with N-deoxyfructosyllysine in glycated albumin (Wu and Cohen, *Biochem Biophys Res Comm* 207:521, 1995). One such molecule is a murine monoclonal antibody, A717, which specifically binds to epitopes containing Amadori glucose adducts that are present on glycated albumin but are not present on nonglycated albumin, and which is disclosed in U.S. Pat. No. 5,223,392 and U.S. Pat. No. 5,518,720. Administration of the murine A717 to diabetic mice prevents the changes in renal structure and function observed in diabetic control mice; namely, increased urine protein excretion, overproduction of matrix macromolecules, and accumulation of glomerular extracellular matrix (Cohen et al *Kidney Int* 45:1673, 1994; Cohen et al, *J Clin Invest* 95:2338, 1995). These properties of murine monoclonal antibodies in a murine model indicate that humanized antibodies with the same specificity for neutralizing the biologic effects of increased glycated albumin would be beneficial in the treatment of human diabetic nephropathy.

Monoclonal antibodies have emerged as therapeutic modalities for various pathological conditions including malignant, cardiovascular and autoimmune disease. However, clinical trials with murine monoclonal antibodies have indicated that administration of murine IgG elicits a brisk human humoral anti-murine immunoglobulin (HAMA) response that can reduce the circulating half-life of the antibody and produce allergic reactions. Almost all of the murine monoclonal antibodies used clinically have provoked HAMA responses, including HAMA against the framework, the isotype and the idiotype of the murine IgG antibodies. Even though severe side-effects are rare in patients with HAMA following treatment with antibody, most investigators take the position that if monoclonal antibodies are to be used therapeutically, reliable methods for avoiding an immune response must be devised. Genetically engineered antibodies are deemed to address these concerns. They can be constructed to have specific effector functions derived from the structures of different classes and isotypes, and new antibody variants with desired properties and minimal side-effects can be created in vitro.

It would therefore be desirable to create a genetically engineered monoclonal antibody that retains the binding specificities of the murine monoclonal A717 but possesses human antibody structural features at the level of immunoglobulin gene sequences.

SUMMARY OF THE INVENTION

The present invention provides genetically engineered immunoglobulins that are capable of reacting with human glycated albumin.

The present invention also provides genetically engineered immunoglobulins which react with glycated albumin but not other proteins.

The present invention thus relates to immunoglobulins formed by recombinant techniques using suitable host cell cultures and which are reactive with an epitope present on glycated albumin but which are insignificantly reactive with other proteins, whether glycated or nonglycated. These immunoglobulins can be readily prepared in pure form. In other aspects, the invention is directed to DNA which encodes the aforementioned immunoglobulins. The DNA sequence can be manipulated to produce chimeras which draw their homology from species which differ from each other. The heavy and light chain DNA sequences can be truncated to produce fragments such as Fab and F(ab')$_2$ or combined to form single-chain molecules (ScFv).

The present invention provides a novel and improved method for treating complications of diabetes.

Another embodiment of the invention achieves the objects of the invention by providing a method for treating complications of diabetes comprising the step of administering to a diabetic patient a therapeutically effective amount of a therapeutic molecule capable of neutralizing the effects of glycated albumin in vivo.

Another embodiment of the invention achieves the objects of the invention by providing a novel and improved method for treating complications of diabetes comprising the step of administering to a diabetic patient a therapeutically effective amount of a therapeutic molecule that prevents the binding of albumin to its unique cell associated receptors.

These and other objects of the invention are achieved by using a genetically engineered immunoglobulin that specifically recognizes glycated residues of albumin. The epitope for these immunoglobulins is in the Amadori construct, which is the form in which the epitope occurs in vivo such that there has been no artificial or other modification that converts the epitope into a borohydride-reduced or advanced glycation end product construct.

DESCRIPTION OF DRAWINGS

FIG. 2 shows a representation of SDS-PAGE of samples from the purification of huA717-ScFv. Lane 1, molecular overnight standards (106 kd, 80 dk, 49.5 kd, 32.5 kd, 27.5 kd, 18.5 kd); Lane 2, whole cell lysate; Lane 3, lysate pellet;

Lane 4, 8M urea extract; Lane 5, Q-Sepharose fraction; Lane 6, S-Sepharose fraction.

DETAILED DESCRIPTION OF THE PREFERRED EMBODIMENTS

The present invention relates to genetically engineered immunoglobulins to glycated albumin. These immunoglobulins are highly useful for the prevention and treatment of complications of diabetes caused by excess glycated albumin in the circulation.

The present invention is based on the principle of specific immunologic recognition and reaction between a monoclonal antibody and the antigenic epitope to which the antibody uniquely and specifically binds. The specificity of binding is conferred by the tertiary structure of the complementarity determining regions (CDRs), in turn dictated by the primary amino acid sequence and encoded for by the nucleotide sequence of the CDRs. The present invention further relates to the creation of genetically engineered immunoglobulins in which at least a portion of the CDRs retaining the binding specificity of the original murine monoclonal antibody are expressed within a construct containing human sequences for the remaining variable and/or constant regions of the light and heavy chains. On the basis of this invention, novel and improved methods are provided for treating complications of diabetes such as those that occur in the kidney, eye and blood vessels.

The term "immunoglobulin" as used in this invention is meant to include all intact molecules as well as fragments thereof, such as Fab, F(ab')$_2$ and ScFv constructs, which are capable of binding glycated albumin.

The term "complementarity determining region" as used in this invention refers to the hypervariable domains of an immunoglobulin that bind deoxyfructosyllysine in glycated human albumin with high affinity and specificity.

The term "chimeric immunoglobulins" as used in this invention refers to those molecules wherein one portion of each of the amino acid sequences of heavy and light chains is homologous to corresponding sequences in a first immunoglobulin, while the remaining sequence of the chains is homologous to corresponding sequences in another immunoglobulin. Typically, in these chimeric immunoglobulins, the CDR's of both light and heavy chains or even the entire variable regions are derived from antibodies of one species of mammals, while the remaining portions are homologous to the sequences derived from another.

Because of the relevance of recombinant DNA techniques to this invention, one need not be confined to the sequences of amino acids found in natural antibodies. Immunoglobulins can be designed to obtain desired characteristics such as improved effector functions and antigen binding.

Administration according to the methods of the present invention is any method which achieves sufficient concentration of the therapeutic molecule to be therapeutically useful. Typically such administration will be by parenteral routes such as by intravenous, subcutaneous or intramuscular injection, but may include oral administration if the molecule is formulated for enteric protection of its peptide integrity. The term therapeutically useful means that the amount of immunoglobulin and the frequency of administration is sufficient to enable neutralization of excess glycated albumin having the epitope for which immunoglobulins of the present invention are specific. Concentrations of antibodies for therapeutic uses will typically be about 1.0 to 10.0 mg, and can be estimated on a mole-mole basis for genetically engineered constructs of different molecular weights to achieve the requisite effective concentrations of glycated albumin-binding power. Frequency of administration of antibodies for therapeutic uses will typically be about once a day to once a week and can be determined empirically by measuring glycated albumin levels.

For purposes of the invention, the glycated albumin target may be present in the circulation.

The above disclosure generally describes the present invention. A more complete understanding can be obtained by reference to the following specific examples which are provided herein for purposes of illustration only, and are not intended to limit the scope of the invention.

Hybridomas producing monoclonal antibodies against glycated albumin can be obtained by standard immunologic techniques. The examples provided herein describe the preparation of a DNA compound with the CDRs of monoclonal antibody A717. Those skilled in the art could produce a DNA compound with the CDRs of other antibodies against glycated albumin. Standard molecular biology techniques and methods as described by Maniatis et al. (Maniatis et al, In: Molecular Cloning: A Laboratory Manual, Cold Spring Harbor Laboratory, Cold Spring Harbor, N.Y., 1982), the text of which is fully incorporated herein by reference, was used throughout.

EXAMPLE 1

Isolation of DNA sequences encoding the A717 heavy and light chain variable regions A mouse hybridoma cell line which secretes anti-glycated albumin antibodies, A717, has been prepared as described by Cohen (U.S. Pat. No. 5,223,392) the text of which is fully incorporated herein by reference, and was used as mRNA source.

Poly A$^+$mRNA was isolated from the A717 hybridoma cells using the Fast Track mRNA kit and methods from Invitrogen (San Diego, Calif.). Briefly, 1.3×10$^8$ cells were harvested and washed with phosphate buffered saline. Lysis buffer was added and the cell pellet was resuspended by homogenization. After a 60 minute incubation at 50° C., the DNA was sheared by passing the lysate through a 20-gauge needle several times. Oligo dT cellulose was added to the lysate and incubated for 60 minutes at room temperature. The oligo dT cellulose with bound mRNA was recovered by centrifugation and washed 3 times with binding buffer and 6 times with low salt wash buffer. The purified mRNA was eluted and ethanol precipitated. Approximately 25 µg mRNA was obtained per 10$^8$ cells.

Immunoglobulin (Ig) specific variable region cDNA was prepared from the mRNA by polymerase chain reaction (PCR) using universal Ig-primers and methods from Novagen (Madison, Wis.). First strand synthesis was performed with 60 ng mRNA, 10 pmol 3'-Ig gamma primer or 3'-Ig kappa primer, deoxynucleoside triphosphates and Moloney murine leukemia virus reverse transcriptase (Promega, Madison, Wis.). Second strand synthesis and amplification was carried out by 1PCR using Taq DNA polymerase (Promega) and the requisite 5'-Ig gamma (G) or kappa (K) primers. Strong PCR amplified bands were identified with IgG-A, C and F primer sets and IgK-B, C, D and F primer sets.

Aliquots from each positive PCR reaction were ligated into the pT7Blue (R) vector (Novagen) using T4 DNA ligase (Promega). An aliquot from each ligation was used to transform NovaBlue competent *E. coli* cells (Novagen). Transformants were selected by ampicillin resistance. Several clones from each ligation were analyzed for the presence of Ig-insert by restriction enzyme digestion and positive clones were sequenced using the Sequenase version 2.0 kit (Amersham, Arlington Heights, Ill.) and both forward and reverse primers. Immunoglobulin sequences isolated with KB and KC primers corresponded to the endogenous MOPC-21 variant light chain of the Sp 2/0 fusion partner used to generate the A717 hybridoma. Immunoglobulin sequences isolated with the KD and KF primers were identical and represented the A717 light chain variable region. No immunoglobulin sequences were obtained with the GC and GF clones. Immunglobulin sequence isolated with the GA primer represented the A717 heavy chain variable region. The DNA and amino acid sequences of the variable regions of the A717 heavy (SEQ ID No:1) and light (SEQ ID No:2) chains are shown in the Sequence Listing.

EXAMPLE 2

Preparing a recombinant DNA compound encoding humanized A717 heavy and light chain variable The amino acid sequences of the murine A717 antibody were used to search the EMBL and PIR-protein data bases in order to determine the optimal human sequence with which to humanize the A717 antibody. Each framework region (3×VH and 3×VL) was used to search the data bases, and lists of the 50 most homologous human sequences were obtained for each framework region. Lists of the most homologous human sequences to the complete A717 VH and VL sequences were also compiled. For the complete VH and VL sequences, identity with the human sequences were approximately 66% and 60% respectively. The lower percent of identity when using the complete sequence was due to the hypervariable CDR regions. The percent identity for the individual framework regions was higher, ranging from 70–100% and with an average of about 80%. The murine antibody used JH4 and JK2. These are most homologous to human JH6 and JK4. A first generation humanized A717 antibody would contain A717 CDRs, human frameworks, and homologous human J regions. The most homologous humanized sequences to the A717 VH and VL sequences were designated huA717 VH-1 and huA717 VL-1; including the A717 CDR's, the percent identity between A717 and huA717 was 90% for VH and 84% for VL.

A refinement to this basic humanized version was made in the sequence immediately before and after the CDRs. The CDRs themselves were assigned on the basis of sequence homology data. Molecular models of antibodies have shown that actual CDR loops can contain amino acids up to 5 amino acids away from the "Kabat" CDRs (Kabat et al, In: Sequences of Proteins of Immunological Interest. U.S. Department of Health and Human Services, U.S. Government Printing Office, Washington, D.C., 1987). Also, a framework amino acid 4 residues from a CDR can have functional importance (Reichmann et al, *Nature* 332:323, 1988). Therefore, maintaining at least the major amino acid differences (size, charge) within 4 amino acids of the CDRs as murine was considered desirable. The antibody containing these changes was designated huA717 VH-2 and huA717 VL-2. Additionally, all differences within 4 amino acids of the CDRs could be maintained murine. This antibody was designated huA717 VH-3 and huA717 VL-3.

The amino acid sequences of the V-regions were reverse translated using the actual A717 codons wherever possible and A717 codon preferences everywhere else. Since bacterial expression of humanized antibody fragments was anticipated, bacterial codon preferences were checked for each codon. Those codons with a poor bacterial preference were changed to a codon used by both bacteria and mammalian cells. Unique restriction enzyme sites were engineered in the sequence at approximately 75 base pair intervals by making use of the degeneracy of the genetic code. Alternate VH and VL sequences were generated by incorporating mixed base sites into the sequences during synthesis. Since the number of different sequences generated is equal to $2^N$ (N=number of mixed base positions), only 4 mixed base sites per variable region were incorporated. This produced 16 different sequences for each variable region. Codons were chosen such that restriction enzyme sites would be present or absent depending on the base incorporated. In this way, clones were screened by restriction enzyme analysis to identify particular sequences. Finally, convenient restriction sites 5' and 3' of the coding region of A717 were identified and this flanking sequence was incorporated into the final humanized sequence that was synthesized.

The light and heavy chain V regions of the humanized A717 antibody were synthesized completely as fragments consisting of 8–12 overlapping (10–15 nucleotides) oligomers (70–90 nucleotides). The oligomers for each chain were mixed in equimolar concentrations and kinased. Oligomers were then heated to 95° C. for 2 minutes and cooled to room temperature slowly over 3–4 hours to effectuate annealing. The annealed, kinased oligomers were ligated with T4 ligase into pUC-18, previously cut with Eco RI and Hind III, at a 3-fold molar excess of oligomers to vector. NovaBlue competent *E. coli* cells were transformed with an aliquot of the ligation mixture and plated onto L-broth plates containing 50 μg/ml ampicillin. Transformants were isolated and analyzed for the presence of pUC18-V region plasmid by restriction ene digestion of miniprep DNA. Positive clones were sequenced by the Sanger dideoxynuleotide method using universal forward and reverse primers to verify accuracy of synthesis and to identify the variant sequences synthesized. The DNA and amino acid sequences of the humanized variable regions of the A717 heavy and light chains (huA717 VL-1, SEQ ID No:3; huA717 VH-1, SEQ ID No:4) are shown in the Sequence Listing.

EXAMPLE 3

Construction of the huA717-ScFv

Figure 1:
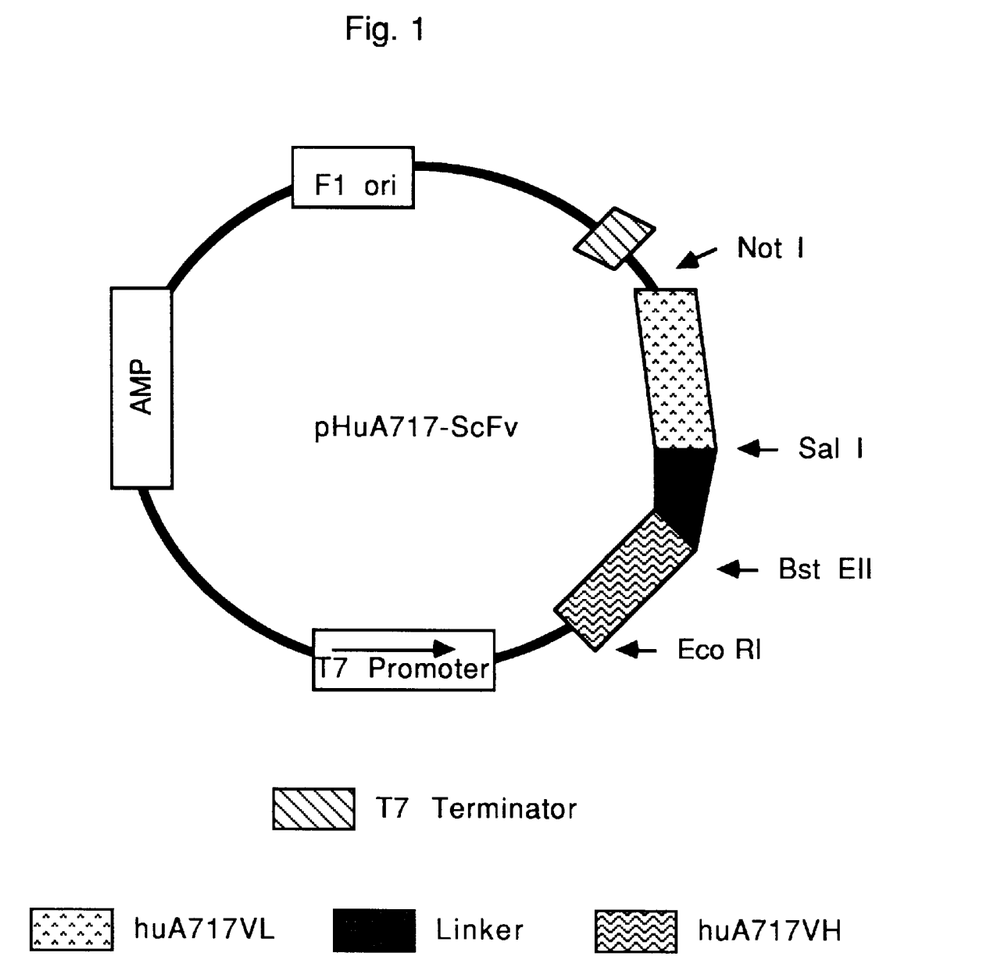
FIG. 1 shows a representation of the expression vector for the humanized A717 single-chain Fv fragment.

A single chain totally humanized A717 antibody gene was constructed from the A717 V-regions of Example 2. The single chain molecule is composed of both the heavy and light chain V-regions separated by a flexible linker region of 13 amino acids. The bacterial expression vector contained T7 expression elements and an internal initiation site to allow direct expression of a cloned gene rather than as a fusion protein. The gene to be expressed was cloned into this vector using a unique Eco RI site on the 5'-end and a Not I site on the 3'-end. PCR primers were synthesized to incorporate an Eco RI site on the 5'-end of the heavy chain V-region and a Bst EII site on the 3'-end. Similarly for the light chains a Sal I site was incorporated on the 5'-end and a Not I site on the 3'-end. The linker fragment was synthesized with a Bst EII site on the 5'-end and a Sal I site on the 3'-end. A four piece ligation into the expression vector yielded the expression construct of heavy chain V-linkerlight chain V. The DNA and amino acid sequences of huA717-ScFv (SEQ ID No:5) is shown in the Sequence Listing. The expression construct is shown in FIG. 1.

Either the A717 V-regions from Example 1 or Example 2 can be cloned into expression vectors containing the human kappa constant gene; the entire human gamma constant gene (for IgG); the human gamma constant gene truncated by a stop codon at amino acid #234 (Kabat et al; for F(ab')$_2$) or the human gamma constant gene with a stop codon at amino acid #224 (Kabat et al; for Fab).

EXAMPLE 4

Expression of huA717-ScFv

Figure 2:
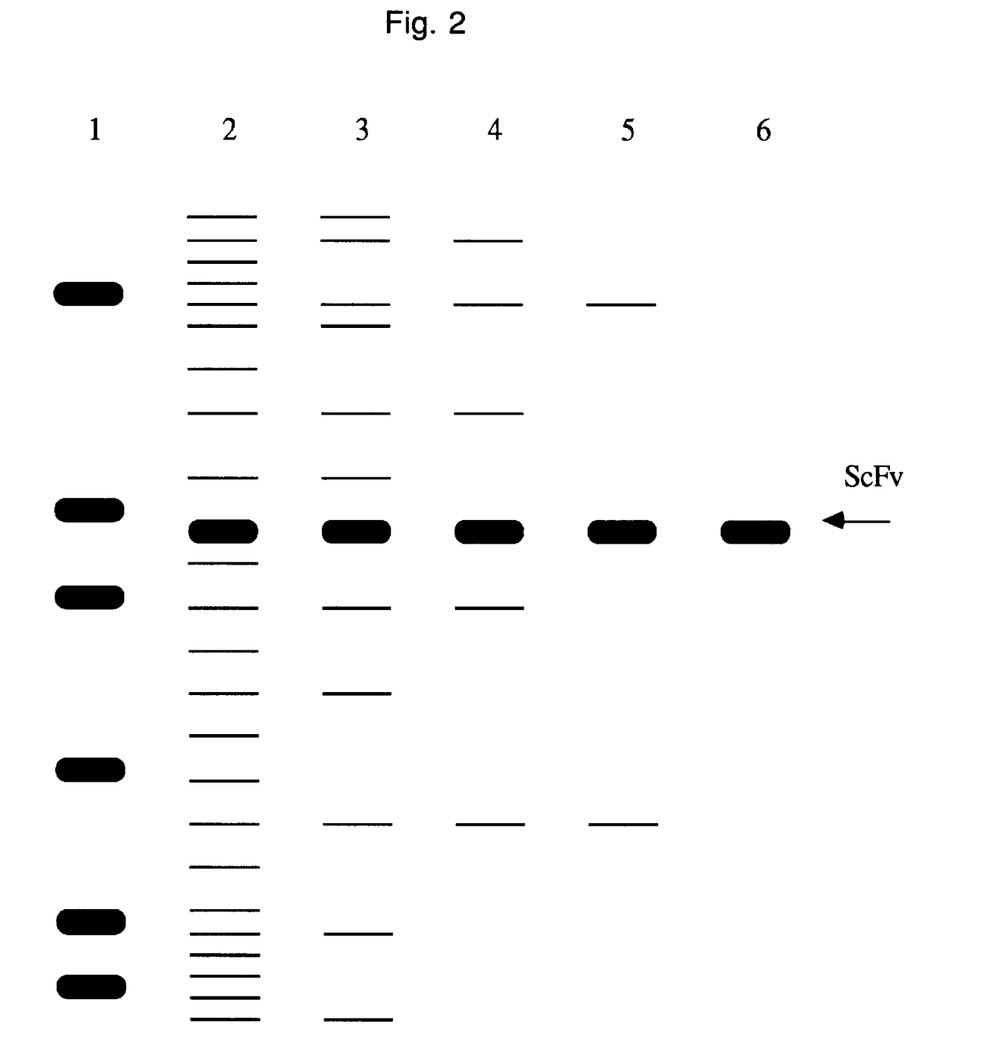

The single chain expression vector (Example 3, above) was transfected into BL21 (DE3) competent cells. This expression host contains the T7 RNA polymerase gene for expression of target proteins under the control of the T7 promoter. In this system, expression is induced with isopropylthio-β-galactoside (IPTG). Transformants were isolated and analyzed for the presence of the expression plasmid by restriction enzyme analysis. Positive clones were grown in the presence of IPTG and expression of huA717-ScFv was monitored by SDS-PAGE. Expression was estimated at approximately 15% of total protein. The huA717-ScFv had an apparent Molecular Weight of 27,000 daltons (FIG. 2).

A chimeric A717 kappa constant gene vector (Example 3, above) can be co-transfected with a chimeric A717 gamma constant gene vector (Example 3, above) into suitable host cells to produce either CDR or variable murine-human chimeric Fab, F(ab')$_2$ or IgG immunoglobulins with the specificity of A717.

EXAMPLE 5

Purification of huA717-ScFv 10 ml of an overnight culture of huA717-1 ScFv (BL21-DE3) was added to 1 liter of L-Broth containing 50 μg/ml ampicillin. The culture was grown at 37° C. with shaking for about 3 hours until the O.D. 600 was about 0.6. IPTG was added to 0.5 mM and the culture was induced for 16 hours. The cells were pelleted by centrifugation at 1000×g for 15 minutes and washed with 50 ml of lysis buffer (50 mM Tris, 100 mM NaCl, 1.0 mM DTT, pH 8.5). The cells were resuspended in 2 ml of the same buffer. Lysozyme was added to 200 μg/ml and the suspension was incubated at room temperature for 30 minutes. The sample was then sonicated 4 times for 15 seconds each with cooling. The volume was adjusted to 10 ml with lysis buffer and sodium deoxycholate was added to 0.2%. Inclusion bodies were pelleted at 1000×g for 15 minutes and washed with 10 ml of lysis buffer containing 0.5% Triton X-100, followed by 2 washes with 10 ml of lysis buffer. The final pellet was weighed and solubilized with 8M urea in lysis buffer at pH 10.5 using 200 ml per gram wet weight of inclusion bodies (about 0.5 mg/ml protein). The sample was refolded by dialysis against lysis buffer containing progressively less urea over a 72 hour period. Final dialysis was against 20 mM sodium carbonate, pH=8.5. Precipitated material was removed by centrifugation and the supernatant was passed over a O-Sepharose column. Protein was eluted using a 0–300 mM NaCl gradient in 20 mM sodium carbonate, pH=8.5. Peak fractions were analyzed by SDS-PAGE and fractions containing hu A717-single chain were pooled, brought to 50 mM sodium acetate pH=5, dialyzed against 20 mM sodium acetate, pH=5, and applied to a S-Sepharose column. Protein was eluted with 0–500 mM NaCl gradient in 20 mM sodium acetate, pH=5. Peak fractions were analyzed by SDS-PAGE and fractions containing hu A717-single chain were pooled and dialyzed against PBS. FIG. 2 shows a SDS-PAGE gel of samples during the purification process.

EXAMPLE 6

Specificity and affinity of huA717-ScFv for authentic gylcated albumin

Figure 3:
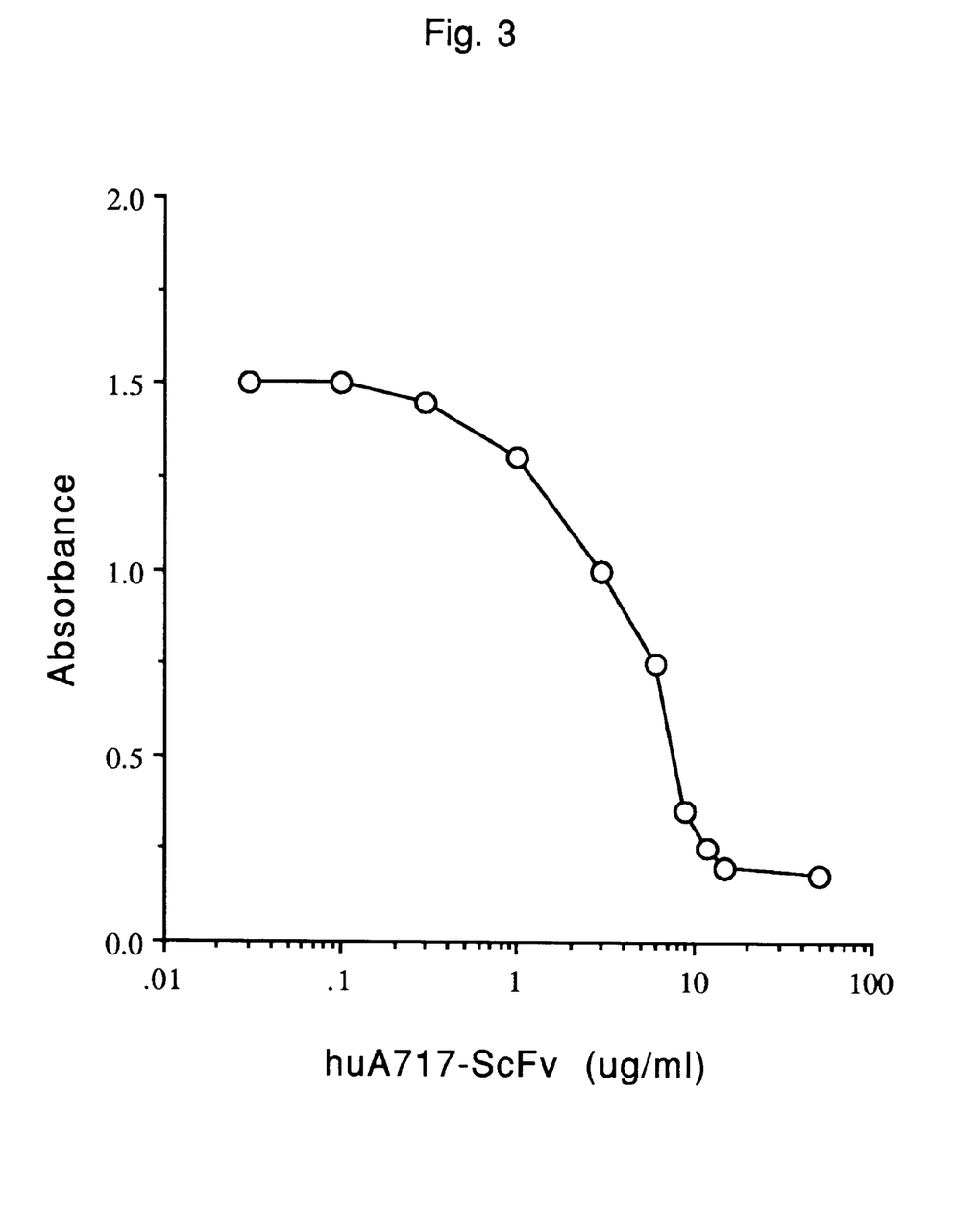
FIG. 3 shows the results of a competition experiment indicating the ability of huA717-ScFv to compete with A717-Fab for binding to glycated albumin.

The relative affinity of huA717-ScFv for authentic glycated albumin was measured in a competitive binding assay. Microtiter wells were coated with glycated albumin, and various dilutions of huA717-ScFv were added to the wells along with 5 μg of murine A717 Fab fragment, and incubated for one hour at 37° C. The plates were washed and then HRP-conjugated anti-murine Fab antibody was added to the wells and incubated for 1 hour at 37° C. The plates were washed, developed with TMB, the reaction stopped, and absorbance read at 450 nm. Approximately 6 μg of huA717-ScFv single chain was required for 50% inhibition of murine Fab binding (FIG. 3). On a molar basis, 200 pmol of huA717-ScFv was required to prevent 50 pmol of murine A717 Fab from binding to glycated albumin. This represented an approximately 4-fold decrement in relative affinity of huA717-ScFv for glycated albumin compared with the murine A717 Fab. Since decreases of affinity ranging from 3–10 fold during the humanization process are expected, in this context the activity of huA717-ScFv is quite good.

Figure 4:
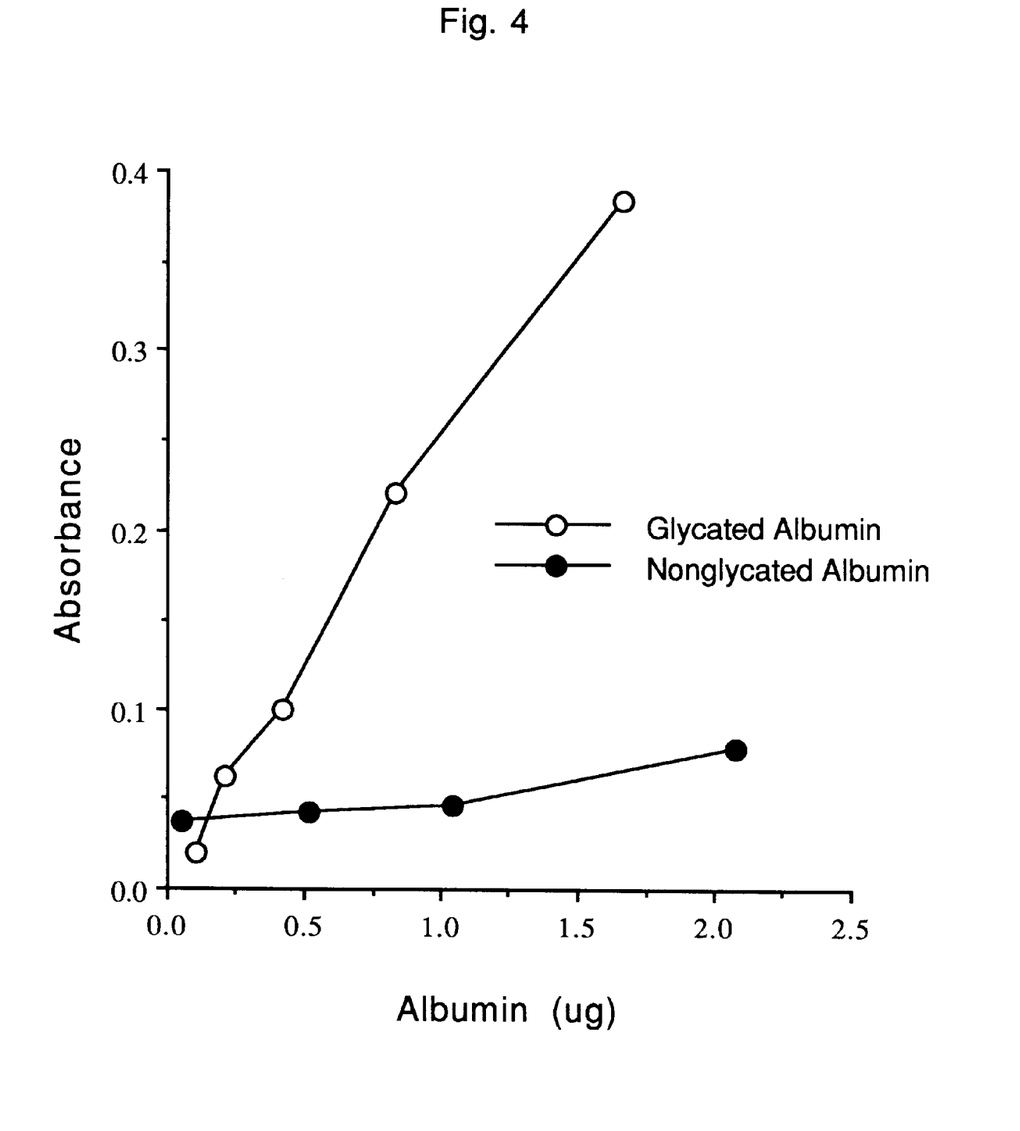
FIG. 4. shows the specificity of huA717-ScFv for glycated albumin but not nonglycated albumin.

Binding specificity was demonstrated with a direct binding assay in which the humanized A717-ScFv was coated onto microtiter wells, which were washed and blocked. Varying concentrations of glycated or nonglycated proteins were added and incubated for 1 hour at 37° C. After washing, HRP conjugated secondary antibody was added and incubated for 1 hour at 37° C. After washing, TMB color developer was added, followed by color stopper, and absorbances were read at 450 nm. The humanized A717-ScFv was shown to react dose responsively with glycated albumin, but not with deglycated albumin (FIG. 4) or with other plasma proteins, whether glycated or not.

I claim:

1. An isolated DNA molecule that comprises DNA encoding an IgG molecule having specificity for glycated albumin as defined by a monoclonal antibody produced by cell line ATCC 9596 and comprising a complementarity determining region of murine origin, a variable framework region of human origin (Seq Id. No: 3,4) and a constant region of human origin.

2. An isolated DNA molecle that comprises DNA encoding an immunoglobulin F(ab')$_2$ molecule having specificity for glycated albumin as defined by a monoclonal antibody produced by cell line ATCC 9596 and comprising a complementarity determining region of murine origin, a variable framework region of human origin (Seq Id. No: 3,4) and a constant region of human origin.

3. An isolated DNA molecule that comprises DNA encoding in immunoglobulin Fab molecule having specificity for glycated albumin as defined by a monoclonal antibody produced by cell line ATCC 9596 and comprising a complementarity determining region of murine origin, a variable framework region of human origin (Seq Id. No: 3,4) and a constant region of human origin.

4. An isolated DNA molecule that comprises DNA encoding a single chain immunoglobulin (ScFv) molecule having specificity for glycated albumin as defined by a monoclonal antibody produced by cell line ATCC 9596 and comprising a complementarity determining region of murine origin and a variable framework region of human origin (Seq Id. No: 5).

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
    (A) LENGTH: 360 base pairs/120 amino acid residues
    (B) TYPE: nucleic acid/amino acid
    (C) STRANDEDNESS: double stranded
    (D) TOPOLOGY: linear (ii) MOLECULE TYPE: cDNA to mRNA
    (A) DESCRIPTION: A717 immunoglobulin heavy chain variable
        region (iii) HYPOTHETICAL: no (iv) ANTI-SENSE: no (v) FRAGMENT TYPE: N-terminal (vi) ORIGINAL SOURCE: A717 hybridoma cell line
    (A) ORGANISM: murine
    (B) STRAIN: Balb/c
    (C) INDIVIDUAL ISOLATE: immunized with human glycated albumin
    (D) DEVELOPMENTAL STAGE: N/A
    (E) HAPLOTYPE: N/A
    (F) TISSUE TYPE: lymphoid, spleen
    (G) CELL TYPE: B-cell
    (H) CELL LINE: fused to Sp2/0 murine hybridoma cell line
    (I) ORGANELLE: N/A (vii) IMMEDIATE SOURCE: plasmid
    (A) LIBRARY: N/A
    (B) CLONE: pA717VH (viii) POSITION IN GENOME:
    (A) CHROMOSOME/SEGMENT: unknown
    (B) MAP POSITION: unknown
    (C) UNITS: unknown (ix) FEATURE: antigen binding sites
    (A) NAME/KEY:      CDR-1;    CDR-2;    CDR-3
    (B) LOCATION: aa #31-35; aa#50-66; aa#99-109
    (C) IDENTIFICATION METHOD: similarity to known sequences
    (D) OTHER INFORMATION: antigen is human glycated albumin (x) PUBLICATION INFORMATION: N/A
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:1:

(xi) SEQUENCE DESCRIPTION: SEQ ID NO:1:

```
GAG GTG CAG CTG GTG GAG TCT GGG GGA GGC TTA GTG CAG CCT GGA GGG         48
Glu Val Gln Leu Val Glu Ser Gly Gly Gly Leu Val Gln Pro Gly Gly
 1               5                  10                  15

TCC CTG AAA CTC TCC TGT GCA GCC TCT GGA TTC ACT TTC AGT TTC TAT         96
Ser Leu Lys Leu Ser Cys Ala Ala Ser Gly Phe Thr Phe Ser Phe Tyr
                20                  25                  30

GGC ATG TCT TGG GTT CGC CAG ACT CCA GAC AAG AGG CTG GAG TTG GTC        144
Gly Met Ser Trp Val Arg Gln Thr Pro Asp Lys Arg Leu Glu Leu Val
        35                  40                  45

GCA ACC ATT AAT AGT AAT GGT GTT AAC ACC TAT TAT CCA GAC AGT GTG        192
Ala Thr Ile Asn Ser Asn Gly Val Asn Thr Tyr Tyr Pro Asp Ser Val
50                  55                  60

AAG GGC CGA TTC ACC ATC TCC AGA GAC AAT GCC AAG AAC ACC CTG TAC        240
Lys Gly Arg Phe Thr Ile Ser Arg Asp Asn Ala Lys Asn Thr Leu Tyr
65                  70                  75                  80

CTG CAA TTG AGC AGT CTG AAG TCT GAG GAC ACA GCC ATG TAT TAC TGT        288
Leu Gln Leu Ser Ser Leu Lys Ser Glu Asp Thr Ala Met Tyr Tyr Cys
            85                  90                  95
```

```
GCA AGA GAT GGT TAC CTT TAT TAC TAT GCT ATG GAC TAC TGG GGT CAA      336
Ala Arg Asp Gly Tyr Leu Tyr Tyr Tyr Ala Met Asp Tyr Trp Gly Gln
            100                 105                 110

GGA ACC TCA GTC ACC GTC TCC TCA                                      360
Gly Thr Ser Val Thr Val Ser Ser
        115                 120

(2) INFORMATION FOR SEQ ID NO:2:

(i) SEQUENCE CHARACTERISTICS:
        (A) LENGTH:  321 base pairs/107 amino acid residues
        (B) TYPE:  nucleic acid/amino acid
        (C) STRANDEDNESS:  double stranded
        (D) TOPOLOGY:  linear (ii) MOLECULE TYPE:  cDNA to mRNA
        (A) DESCRIPTION:  A717 immunoglobulin light chain variable
            region (iii) HYPOTHETICAL:  no (iv) ANTI-SENSE:  no (v) FRAGMENT TYPE:  N-terminal (vi) ORIGINAL SOURCE:  A717 hybridoma cell line
        (A) ORGANISM:  murine
        (B) STRAIN:  Balb/c
        (C) INDIVIDUAL ISOLATE:  immunized with human glycated albumin
        (D) DEVELOPMENTAL STAGE:  N/A
        (E) HAPLOTYPE:  N/A
        (F) TISSUE TYPE:  lymphoid, spleen
        (G) CELL TYPE:  B-cell
        (H) CELL LINE:  fused with Sp2/0 hybridoma cell line
        (I) ORGANELLE:  N/A (vii) IMMEDIATE SOURCE:  plasmid
        (A) LIBRARY:  N/A
        (B) CLONE:  pA717VL (viii) POSITION IN GENOME:
        (A) CHROMOSOME/SEGMENT:  unknown
        (B) MAP POSITION:  unknown
        (C) UNITS:  unknown (ix) FEATURE:  antigen binding sites
        (A) NAME/KEY:     CDR-1;     CDR-2;     CDR-3
        (B) LOCATION:  aa#24-34; aa#50-56; aa#89-97
        (C) IDENTIFICATION METHOD:  similarity to known sequences
        (D) OTHER INFORMATION:  antigen is human glycated albumin (x) PUBLICATION INFORMATION:  N/A
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:2:

(xi) SEQUENCE DESCRIPTION: SEQ ID NO:2:

GAC ATC AAG ATG ACC CAG TCT CCA TCT TCC ATG TAT GCA TCT CTA GGA       48
Asp Ile Lys Met Thr Gln Ser Pro Ser Ser Met Tyr Ala Ser Leu Gly
  1               5                  10                  15

GAG AGA GTC ACT ATC ACT TGC AAG GCG AGT CAG GAC ATT GAT AGC TAT       96
Glu Arg Val Thr Ile Thr Cys Lys Ala Ser Gln Asp Ile Asp Ser Tyr
             20                  25                  30

TTA AGC TGG TTC CAG CAG AAA CCA GGG AAT TCT CCT AAG ACC CTG ATC      144
Leu Ser Trp Phe Gln Gln Lys Pro Gly Asn Ser Pro Lys Thr Leu Ile
         35                  40                  45
```

```
TAT CAT ACA AAC AGA TTG TTA GAT GGG GTC CCA TCA AGG TTC AGT GGC        192
Tyr His Thr Asn Arg Leu Leu Asp Gly Val Pro Ser Arg Phe Ser Gly
    50                  55                  60

AGT GGA TCT GGA CAA GAT TAT TCT CTC ACC ATC AGC AGC CTG GAG TAT        240
Ser Gly Ser Gly Gln Asp Tyr Ser Leu Thr Ile Ser Ser Leu Glu Tyr
65                  70                  75                  80

GAA GAT ATG GGA ATT TAT TAT TGT CTA CAG TAT GAT GAG TTT CCT CCC        288
Glu Asp Met Gly Ile Tyr Tyr Cys Leu Gln Tyr Asp Glu Phe Pro Pro
                85                  90                  95

ACG TTC GGA GGG GGG ACC AAG CTG GAA ATA AAA                            321
Thr Phe Gly Gly Gly Thr Lys Leu Glu Ile Lys
                100                 105
```

(2) INFORMATION FOR SEQ ID NO:3:

(i) SEQUENCE CHARACTERISTICS:
        (A) LENGTH:  360 base pairs/120 amino acid residues
        (B) TYPE:  nucleic acid/amino acid
        (C) STRANDEDNESS:  double stranded
        (D) TOPOLOGY:  linear     (ii) MOLECULE TYPE:  other nucleic acid
        (A) DESCRIPTION:  humanized A717 heavy chain variable region     (iii) HYPOTHETICAL:  yes     (iv) ANTI-SENSE:  no     (v) FRAGMENT TYPE:  N-terminal     (vi) ORIGINAL SOURCE:  synthetic
        (A) ORGANISM:  N/A
        (B) STRAIN:  N/A
        (C) INDIVIDUAL ISOLATE:  N/A
        (D) DEVELOPMENTAL STAGE:  N/A
        (E) HAPLOTYPE:  N/A
        (F) TISSUE TYPE:  N/A
        (G) CELL TYPE:  N/A
        (H) CELL LINE:  N/A
        (I) ORGANELLE:  N/A     (vii) IMMEDIATE SOURCE:  plasmid
        (A) LIBRARY:  N/A
        (B) CLONE:  pHuA717VH-1

(viii) POSITION IN GENOME:  N/A
        (A) CHROMOSOME/SEGMENT:
        (B) MAP POSITION:
        (C) UNITS:

(ix) FEATURE:  human framework regions; murine CDRs
        (A) NAME/KEY:  FR-1; CDR-1; FR-2; CDR-2;FR-3;CDR-3;FR-4
        (B) LOCATION:  aa#1-30; aa#31-35; aa#36-49; aa#50-66;
            aa#67-98; aa#99-109; aa#110-120
        (C) IDENTIFICATION METHOD:  similarity to known sequences
        (D) OTHER INFORMATION:  antigen is human glycated albumin     (x) PUBLICATION INFORMATION:  N/A
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:3:

(ix) SEQUENCE DESCRIPTION:  SEQ ID NO:3:

```
GAG GTG CAG CTG GTG GAG TCT GGG GGA GGC TTA GTG CAG CCT GGA GGG        48
Glu Val Gln Leu Val Glu Ser Gly Gly Gly Leu Val Gln Pro Gly Gly
1               5                   10                  15
```

```
TCC CTG AGA CTC TCC TGT GCA GCC TCT GGA TTC ACT TTC AGT TTC TAC          96
Ser Leu Arg Leu Ser Cys Ala Ala Ser Gly Phe Thr Phe Ser Phe Tyr
            20                  25                  30

GGC ATG TCT TGG GTT CGC CAG GCG CCT GGC AAA GGG CTG GAA TGG GTC         144
Gly Met Ser Trp Val Arg Gln Ala Pro Gly Lys Gly Leu Glu Trp Val
        35                  40                  45

GCA ACC ATT AAT AGT AAT GGT GTT AAC ACC TAT TAT CCA GAC AGT GTG         192
Ala Thr Ile Asn Ser Asn Gly Val Asn Thr Tyr Tyr Pro Asp Ser Val
    50                  55                  60

AAG GGC CGA TTC ACC ATC TCC AGA GAC AAT TCG AAG AAC ACG TTG TAC         240
Lys Gly Arg Phe Thr Ile Ser Arg Asp Asn Ser Lys Asn Thr Leu Tyr
65                  70                  75                  80

CTG CAA ATG AAC AGT CTG AGG GCT GAG GAC ACA GCC GTG TAT TAC TGT         288
Leu Gln Met Asn Ser Leu Arg Ala Glu Asp Thr Ala Val Tyr Tyr Cys
                85                  90                  95

GCA AGA GAT GGT TAT CTT TAT TAC TAT GCT ATG GAC TAC TGG GGT CAA         336
Ala Arg Asp Gly Tyr Leu Tyr Tyr Tyr Ala Met Asp Tyr Trp Gly Gln
            100                 105                 110

GGA ACC ACA GTC ACC GTC TCC TCA                                         360
Gly Thr Thr Val Thr Val Ser Ser
        115                 120
```

(2) INFORMATION FOR SEQ ID NO:4:

(i) SEQUENCE CHARACTERISTICS:
        (A) LENGTH: 321 base pairs/107 amino acid residues
        (B) TYPE: nucleic acid/amino acid
        (C) STRANDEDNESS: double stranded
        (D) TOPOLOGY: linear     (ii) MOLECULE TYPE: other nucleic acid
        (A) DESCRIPTION: humanized A717 light chain variable region     (iii) HYPOTHETICAL: yes     (iv) ANTI-SENSE: no     (v) FRAGMENT TYPE: N-terminal     (vi) ORIGINAL SOURCE: synthetic
        (A) ORGANISM: N/A
        (B) STRAIN: N/A
        (C) INDIVIDUAL ISOLATE: N/A
        (D) DEVELOPMENTAL STAGE: N/A
        (E) HAPLOTYPE: N/A
        (F) TISSUE TYPE: N/A
        (G) CELL TYPE: N/A
        (H) CELL LINE: N/A
        (I) ORGANELLE: N/A     (vii) IMMEDIATE SOURCE: plasmid
        (A) LIBRARY: N/A
        (B) CLONE: pHuA717VL-1

(viii) POSITION IN GENOME: N/A
        (A) CHROMOSOME/SEGMENT:
        (B) MAP POSITION:
        (C) UNITS:

(ix) FEATURE: human framework regions; A717 CDRs
        (A) NAME/KEY: FR-1;CDR-1;FR-2;CDR-2;FR-3;CDR-3;FR-4
        (B) LOCATION: aa#1-23; aa#24-34; aa#35-49; aa#50-56;
            aa#57-88; aa#89-97; aa#98-107
        (C) IDENTIFICATION METHOD: similarity to known sequences
        (D) OTHER INFORMATION: antigen is human glycated albumin     (x) PUBLICATION INFORMATION: N/A
        (A) AUTHORS:
        (B) TITLE:
        (C) JOURNAL:
        (D) VOLUME:
        (E) ISSUE:

```
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:4:

(xi) SEQUENCE DESCRIPTION: SEQ ID NO:4:

GAT ATC CAG ATG ACC CAG TCT CCA TCT TCC TTG TCT GCA TCT GTA GGA          48
Asp Ile Gln Met Thr Gln Ser Pro Ser Ser Leu Ser Ala Ser Val Gly
 1               5                  10                  15

GAT AGA GTC ACT ATC ACG TGC AAG GCG AGT CAG GAC ATT GAT AGC TAT          96
Asp Arg Val Thr Ile Thr Cys Lys Ala Ser Gln Asp Ile Asp Ser Tyr
             20                  25                  30

TTA AGC TGG TTT CAG CAG AAA CCC GGG AAA GCT CCT AAG TCA CTG ATC         144
Leu Ser Trp Phe Gln Gln Lys Pro Gly Lys Ala Pro Lys Ser Leu Ile
         35                  40                  45

TAT CAT ACA AAC AGA TTG TTA GAT GGG GTG CCA TCT AGA TTC AGT GGC         192
Tyr His Thr Asn Arg Leu Leu Asp Gly Val Pro Ser Arg Phe Ser Gly
     50                  55                  60

AGT GGA TCT GGA ACA GAT TTT ACT CTC ACC ATC AGC AGC CTG CAG CCT         240
Ser Gly Ser Gly Thr Asp Phe Thr Leu Thr Ile Ser Ser Leu Gln Pro
 65              70                  75                  80

GAG GAT TTC GCA ACT TAT TAT TGT CTA CAG TAT GAT GAG TTT CCT CCC         288
Glu Asp Phe Ala Thr Tyr Tyr Cys Leu Gln Tyr Asp Glu Phe Pro Pro
             85                  90                  95

ACG TTC GGA GGG GGT ACC AAG GTG GAA ATA AAA                             321
Thr Phe Gly Gly Gly Thr Lys Val Glu Ile Lys
            100                 105

(2) INFORMATION FOR SEQ ID NO:5:

(i) SEQUENCE CHARACTERISTICS:
        (A) LENGTH:  720 base pairs/240 amino acid residues
        (B) TYPE:  nucleic acid/amino acid
        (C) STRANDEDNESS: double stranded
        (D) TOPOLOGY:  linear (ii) MOLECULE TYPE:  other nucleic acid
        (A) DESCRIPTION:  humanized A717 immunoglobulin single-chain
                         Fv (iii) HYPOTHETICAL:  yes (iv) ANTI-SENSE:  no (v) FRAGMENT TYPE:  N-terminal fragment (vi) ORIGINAL SOURCE:  synthetic
        (A) ORGANISM:  N/A
        (B) STRAIN:  N/A
        (C) INDIVIDUAL ISOLATE:  N/A
        (D) DEVELOPMENTAL STAGE:  N/A
        (E) HAPLOTYPE:  N/A
        (F) TISSUE TYPE:  N/A
        (G) CELL TYPE:  N/A
        (H) CELL LINE:  N/A
        (I) ORGANELLE:  N/A (vii) IMMEDIATE SOURCE:  plasmid
        (A) LIBRARY:  N/A
        (B) CLONE:  pHuA717ScFv-1

(viii) POSITION IN GENOME:  N/A
        (A) CHROMOSOME/SEGMENT:
        (B) MAP POSITION:
        (C) UNITS:

(ix) FEATURE:  HuA717VH-1 linked to HuA717VL
        (A) NAME/KEY:   HuA717VH;  linker;  HuA717VL
        (B) LOCATION:  aa# 1-120; aa# 121-133; aa# 134-240
        (C) IDENTIFICATION METHOD:  similarity to known sequences
```

(D) OTHER INFORMATION: antigen is human glycated albumin (x) PUBLICATION INFORMATION: N/A
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:5:

(xi) SEQUENCE DESCRIPTION: SEQ ID NO:5:

```
GAG GTG CAG CTG GTG GAG TCT GGG GGA GGC CTA GTG CAG CCT GGA GGG        48
Glu Val Gln Leu Val Glu Ser Gly Gly Gly Leu Val Gln Pro Gly Gly
 1               5                  10                  15

TCC CTG AGA CTC TCC TGT GCA GCC TCT GGA TTC ACT TTC AGT TTC TAC        96
Ser Leu Arg Leu Ser Cys Ala Ala Ser Gly Phe Thr Phe Ser Phe Tyr
             20                  25                  30

GGC ATG TCT TGG GTT CGC CAG GCG CCT GGC AAA GGG CTG GAA TGG GTC       144
Gly Met Ser Trp Val Arg Gln Ala Pro Gly Lys Gly Leu Glu Trp Val
         35                  40                  45

GCA ACC ATT AAT AGT AAT GGT GTT AAC ACC TAT TAT CCA GAC AGT GTG       192
Ala Thr Ile Asn Ser Asn Gly Val Asn Thr Tyr Tyr Pro Asp Ser Val
     50                  55                  60

AAG GGC CGA TTC ACC ATC TCC AGA GAC AAT TCG AAG AAC ACG TTG TAC       240
Lys Gly Arg Phe Thr Ile Ser Arg Asp Asn Ser Lys Asn Thr Leu Tyr
 65                  70                  75                  80

CTG CAA ATG AAC AGT CTG AGG GCT GAG GAC ACA GCC GTG TAT TAC TGT       288
Leu Gln Met Asn Ser Leu Arg Ala Glu Asp Thr Ala Val Tyr Tyr Cys
                 85                  90                  95

GCA AGA GAT GGT TAT CTT TAT TAC TAT GCT ATG GAC TAC TGG GGT CAA       336
Ala Arg Asp Gly Tyr Leu Tyr Tyr Tyr Ala Met Asp Tyr Trp Gly Gln
            100                 105                 110

GGA ACC ACA GTC ACC GTC TCC TCA GAG GGT AAA TCC TCA GGA TCT GGC       384
Gly Thr Thr Val Thr Val Ser Ser Glu Gly Lys Ser Ser Gly Ser Gly
        115                 120                 125

TCC GAA TCC AAA GTC GAC ATC CAG ATG ACC CAG TCT CCA TCT TCC TTG       432
Ser Glu Ser Lys Val Asp Ile Gln Met Thr Gln Ser Pro Ser Ser Leu
130                 135                 140

TCT GCA TCT GTA GGA GAT AGA GTC ACT ATC ACG TGC AAG GCG AGT CAG       480
Ser Ala Ser Val Gly Asp Arg Val Thr Ile Thr Cys Lys Ala Ser Gln
145                 150                 155                 160

GAC ATT GAT AGC TAT TTA AGC TGG TTT CAG CAG AAA CCC GGG AAA GCT       528
Asp Ile Asp Ser Tyr Leu Ser Trp Phe Gln Gln Lys Pro Gly Lys Ala
                165                 170                 175

CCT AAG TCA CTG ATC TAT CAT ACA AAC AGA TTG TTA GAT GGG GTG CCA       576
Pro Lys Ser Leu Ile Tyr His Thr Asn Arg Leu Leu Asp Gly Val Pro
            180                 185                 190

TCT AGA TTC AGT GGC AGT GGA TCT GGA ACA GAT TTT ACT CTC ACC ATC       624
Ser Arg Phe Ser Gly Ser Gly Ser Gly Thr Asp Phe Thr Leu Thr Ile
        195                 200                 205

AGC AGC CTG CAG CCT GAG GAT TTC GCA ACT TAT TAT TGT CTA CAG TAT       672
Ser Ser Leu Gln Pro Glu Asp Phe Ala Thr Tyr Tyr Cys Leu Gln Tyr
    210                 215                 220

GAT GAG TTT CCT CCC ACG TTC GGA GGG GGT ACC AAG GTG GAA ATA AAA       720
Asp Glu Phe Pro Pro Thr Phe Gly Gly Gly Thr Lys Val Glu Ile Lys
225                 230                 235                 240
```